United States Patent [19]

Herms et al.

[11] Patent Number: 4,817,600
[45] Date of Patent: Apr. 4, 1989

[54] IMPLANTABLE FILTER

[75] Inventors: James K. Herms, Watertown; Gaillard R. Nolan, Acton; Jonathan McGrath, Canton; Mark J Tolkoff, Brookline, all of Mass.

[73] Assignee: Medi-Tech, Inc., Watertown, Mass.

[21] Appl. No.: 53,354

[22] Filed: May 22, 1987

[51] Int. Cl.$^4$ ............................................. A61B 17/00
[52] U.S. Cl. .................................. 128/303 R; 128/345
[58] Field of Search .................. 128/1 R, 303 R, 325, 128/345

[56] References Cited

U.S. PATENT DOCUMENTS

| | | | |
|---|---|---|---|
| 2,281,448 | 4/1942 | Mathey . | |
| 3,334,629 | 8/1967 | Cohn | 128/325 R |
| 3,540,431 | 11/1970 | Mobin-Uddin . | |
| 3,786,807 | 1/1974 | Dubin . | |
| 3,952,747 | 8/1976 | Kimmel | 128/303 R |
| 4,425,908 | 1/1984 | Simon | 128/1 R |
| 4,494,531 | 1/1985 | Gianturco | 128/1 R |
| 4,619,246 | 10/1986 | Nielsen et al. | 128/345 X |
| 4,643,184 | 2/1987 | Vodin | 128/303 R |
| 4,688,553 | 8/1987 | Metals | 128/325 X |

FOREIGN PATENT DOCUMENTS 0188927 7/1986 European Pat. Off. .
2573646 5/1986 France .
2570288 5/1986 France .

OTHER PUBLICATIONS

Gunther et al., Fortschr. Rontgenstr., "Animal experiments with a new cava filter", vol. 142 No. 2, pp. 208-212 (1985).
Lund et al., Radiology, "Retrievable vena cava filter percutaneously introduced", vol. 155, No. 3, p. 831 (1985).
Lund et al., Radiology, "A new vena caval filter for percutaneous placement and retrieval: experimental study", vol. 152, pp. 369-372 (9/29/84).
Tadavarthy et al., Radiology, "Kimray-Greenfield vena cava filter: percutaneous introduction", vol. 151 No. 2, pp. 525-526 (1984).
Jarrell et al., Surg., Gyn. & Obstet., "A new method of management using the Kim-Ray Greenfield filter for deep venous thrombosis and pulmonary embolism in spinal cord injury", 157:316 (10/83).
Cragg et al., AJR, "A new percutaneous vena cava filter", vol. 141, pp. 601-604 (9/83).
Peyton et al., Surgery, "Comparison of Greenfield filter and vena caval ligation for experimental septic thromboembolism", pp. 533-537 (4/83).
Scurr et al., Annals of the Royal College of Surgeons of England, "The treatment of recurrent pulmonary embolism: experience with the Kimray Greenfield vena cava filter", vol. 65, pp. 233-234 (1983).
Palestrant et al., Radiology, "Comparative in vitro evaluation of the nitinol vena cava filter", vol. 145 No. 2, pp. 351-355, (11/82).

(List continued on next page.)

Primary Examiner—Stephen C. Pellegrino

[57] ABSTRACT

A blood clot filtration device, for implantation percutaneously, for preventing movement of blood clots within a blood vessel. The device has a head and a plurality of legs extending therefrom. The legs include a first linear leg portion of predetermined length emanating distally from the head generally parallel to the axis of the device; a second multi-angled leg portion of relatively greater length extending generally outwardly from the distal end of the first linear leg portion at an acute angle to the axis, to form, with other second leg portions, a conical aspect, the second leg portion having a series of discrete linear segments arrayed generally tangent to a cone defined by the second leg portions of the set of legs; and a hook portion at the distal end of each the leg extending outwardly, away from the axis in a manner for engaging the blood vessel to fix the position of the device therewithin. The configuration of the legs, including the first linear portion, and the use of a high strength titanium alloy for the head, formed by fusing, and legs produces a filter which is able to tolerate severe compression for introduction percutaneously through a small sheath without yielding. Preferably a central wire segment is disposed axially, with the first linear leg portions of the filter disposed closely thereabout.

18 Claims, 5 Drawing Sheets

OTHER PUBLICATIONS

Dedrick et al., Interventional Radiology, "Transvenous interruption of the inferior vena cava", (chapter 26, pp. 355–369), "Transvenous pulmonary embolectomy", (chapter 27, pp. 370–373) (6/82).

Cimochowski et al., J. Thorac. Cardiovasc. Surg., "Greenfield filter versus mobin-uddin embrella", vol. 79, pp. 358–365 (1980).

Korwin et al., Arch. Surg., "Prophylactic interruption of the inferior vena cava", vol. 114, pp. 1037–1040 (9/79).

Atik et al., Arch. Surg., "The impact of prophylactic measures on fatal pulmonary embolism", vol. 114, pp. 366–368, (4/79).

Greenfield, World J. Surg., "Intraluminal techniques for vena caval interruption and pulmonary embolectomy", vol. 2 No. 1, pp. 45–59, (1/78).

Blumenberg et al., The Am. J. of Surg., "Long-term follow-up of vena caval clips and umbrellas", vol. 134, pp. 205–208, (8/77).

Driller et al., Med. and Biol. Eng., "New percutaneous caval filter device for pulmonary thromboembolism", pp. 629–635 (11/76).

Lawrence et al., The Am. J. of Surg., "An evaluation of the mobin-uddin umbrella in the prevention of pulmonary thromboembolism", vol. 132, pp. 204–208, (8/76).

Greenfield, CPS, "Pulmonary embolism: diagnosis and management" (1976).

Brown et al., "Experimental comparison of a new intracaval filter with the mobin-uddin umbrella device", pp. 272–276 (8/74).

Knight et al., Radiology, "Percutaneous introduction of inferior vena cava filter: human experience", vol. 111, pp. 61–63 (4/74).

Greenfield et al., Surgery, "A new intracaval filter permitting continued flow and resolution of emboli", vol. 73 No. 1, pp. 599–606 (4/73).

Elkins et al., J. OK. ST. Med. Assoc., "Clinical results with an prothesis and description of a new intracaval filter", pp. 53–59 (2/73).

Fadali et al., Surgery, "A filtering device for the prevention of particulate embolization during the course of cardiac surgery", vol. 64, No. 3, pp. 634–639 (9/68).

MediTech Greenfield, Vena Cava Filter System, 3 piece Advertisement (rev. 2/83).

Cook Inc., Advertisement, Cook "Bird's Nest" Vena Cava Filter.

L. G. Medical s.a., Advertisement, Vena Cava Filter, SP 2000, SP 2010, SP.

Cook, Advertisement, Gunther Vena Cava Filter Set.

Clesa, Advertisement, Sondes De Stimulation Cardiague.

Castaneda-Zuniga et al., *Seminars in Interventional Radiology*, vol. 3, (09/86).

Tadavarthy et al., *Seminars in Interventional Radiology*, "Percutaneous Introduction of Kimray-Greenfield Filters", vol. 3, 196–204, (09/86).

Wallace et al., *AJR*, "Inferior Vena Cava Stent Filler", vol. 147, pp. 1247–1250, (12/86).

Shetty et al., *Radiology*, "Balloon Dilation of the Femoral Vein Expediting Percutaneous Greenfield Vena Cava Filter Placement", vol. 161, p. 275, (1986).

Denny et al., *AJR*, "Percutaneous Kimray-Greenfield Filter Placement by Femoral Vein Puncture", vol. 145, pp. 827–829, (10/85).

PRIOR ART

PRIOR ART

IMPLANTABLE FILTER

BACKGROUND OF THE INVENTION

This invention relates to blood clot filters of the permanent metallic type, that may be placed in the inferior vena cava, one of the two main veins for returning blood to the heart. Their purpose is to stop large clots or thrombi from traveling, typically from the leg veins, through the inferior vena cava, to the heart. If such clots reach the lungs, they would occlude the flow of blood and possibly lead to death.

Filters of this type are typically formed of fine wire legs attached to a head or nose cone. The wire legs have a conical aspect in order to channel emboli (or clots) toward the center of the filter, to the nose cone near the apex of the filter. The filter thus may trap clots of approximately three millimeters or larger. The clot, depending on its age and nature, may stay permanently in the filter or may be resorbed by the body.

One blood clot filter of particular effectiveness is a prior commercial embodiment of Kimmell U.S. Pat. No. 3,952,747, sold by Medi-Tech Incorporated of Watertown, Mass., under the trademark GREEN-FIELD®. The prior commercial Kimmell filter has stainless steel wire legs extending from a large head. According to Kimmell, the legs are arranged in a conical aspect, each leg bent to form a number of linear segments generally tangent about the conical aspect to increase the filtering effect. When the filter is inserted into a blood vessel, the head and the apex of the cone are positioned downstream in the blood flow. The remote ends of the legs are positioned upstream in the blood flow and are engaged with the vessel wall.

Blood vessel filters have previously been introduced into a vessel surgically, by cutting down to and then into a vein, using surgical blades. The filter, confined within a metallic capsule, has been introduced through a catheter. Once in position, the filter has been dislodged from the capsule using a pusher, and the capsule and attached catheter removed. Typically, the surgical procedure has required two special teams of physicians, including a surgeon and a radiologist, and it is not uncommon for the procedure to take up to 2 hours.

More recently, certain filters have been inserted percutaneously. The advantages of this technique include reduced trauma and shortened operating time. The applicability of this technique has been limited in the case of the preferred Kimmell type of filter.

SUMMARY OF THE INVENTION

The present invention features a filter of the Kimmell type having significant improvement that, e.g., enables its percutaneous introduction over a wide range of patient population and inferior vena cava size. In one aspect the invention features a filter of the type mentioned having a head; a plurality of legs having divergent leg portions, each leg secured at one of its ends to the head, each having securing means on its end distal with respect to the head and at least one generally U-shaped bend intermediate its end, with the improvement that each leg further comprises a first linear leg portion between the head and the divergent leg portion, the first linear leg portion having a predetermined length emanating distally from the head, the first linear leg portion being arranged generally parallel to the axis of the device.

According to another aspect of the invention, first leg portions emanating from the head closely surround a central member, the head being formed of the metal of the ends of the first leg portions and of the central member, the central member serving to provide lateral support when the legs are compressed together.

In preferred embodiments, the legs and the head are formed of a titanium alloy, preferably the alloy being at least 50 percent by weight titanium and the head comprises a bead formed by fusing the legs.

According to another aspect of the invention, with the head comprising a bead formed by fusing the legs, each of the legs comprises: (a) a first linear leg portion of predetermined length emanating distally from the head in a direction upstream of the direction of blood clot movement within the vessel, the first linear leg portion arranged generally parallel to the axis of the device, (b) a second, multi-angled leg portion of relatively greater length than the first linear leg portion, the second, multi angled leg portion extending generally outwardly from the distal end of the first linear leg portion, at an acute angle to the axis to form, with second, multi angled leg portions of other legs, a conical aspect, the second, multi-angled leg portion comprising a series of discrete linear segments arrayed generally tangent to a cone defined by the set of second, multi-angled leg portions, and (c) a hook portion at the distal end of each of the legs, extending outwardly, away from the axis, in a manner for engaging the blood vessel wall to fix the position of the device therewithin, and the legs and the head being formed of a titanium alloy.

In further preferred embodiments of the invention, the diameter of the bead that forms the head is of the order of less than about 3 mm; the diameter of the base of the conical aspect of the device measured at the intersection of the second, multi-angled leg portions and the hook portions is between about 28 and 48 mm, preferably the device is adapted to be introduced into the blood vessel within a tubular cavity of an introducing cartridge, the cavity within which the device is disposed for insertion having an inner diameter of the order of between 3 to 4 mm; the length of the first linear leg portion is of the order of about 0.5 to 2 mm; and the overall length of the device along the axis, within the blood vessel, is of the order of about 50 mm.

According to another aspect of the invention there is provided a blood clot filtration device adapted for implantation percutaneously via a tubular cavity of an introducing cartridge, into a blood vessel of the body, the cavity within which the device is disposed for insertion having an inner diameter between about 2 and 4 mm, the filtration device comprising: a head and a plurality of legs extending therefrom, the head comprising a bead formed by fusing the legs and having a diameter of the order of less than about 3 mm, each of the legs comprising: (a) a first linear leg portion of predetermined length emanating distally from the head in a direction upstream of the direction of blood clot movement within the vessel, the first linear leg portion arranged generally parallel to the axis of the device, the predetermined length being of the order of about 0.5 to 2 mm, (b) a second multi angled leg portion of relatively greater length than the first linear leg portion, the second, multi angled leg portion extending generally outwardly from the distal end of the first linear leg portion, at an acute angle to the axis to form, with the second, multi-angled leg portions of other legs, a conical aspect having a diameter at the base of between about 30 and 50 mm, the second, multi-angled leg portion comprising a series of discrete linear segments arrayed generally tangent to the cone defined by the second, multi-angled leg portions, and (c) a hook portion at the distal end of each leg extending outwardly, away from the axis, in a manner for engaging the blood vessel wall to fix the position of the device therewithin, and the legs and the body being formed of a titanium alloy, the overall axial length of the device in position within the blood vessel being of the order of about 50 mm.

The blood clot filtration device of the invention, without detrimental yielding of the metal or loss of function, can be confined to a very narrow diameter for insertion percutaneously using narrow catheter tubes, e.g., 11 French or 3.7 mm internal diameter; the original conical aspect of the legs is regained even after insertion via the narrow catheter tube; and the legs exert appropriate force against the vessel walls upon positioning.

The filter achieves a filtering efficiency and capacity similar to that of the prior commercial Kimmell filter, retaining thromboemboli large enough to produce clinically significant pulmonary embolism. It passes a sufficient quantity of small thromboemboli to prevent either acute or insidious filter clogging, and permits lysis of the retained thromboemboli. Further, it helps to avoid the generation of new thrombi (or growth of retained emboli) from local stasis or turbulence in venous flow, in a wide range of diameters of inferior vena cavae.

Anchoring of the filter within a cava is achieved using approximating similar forces to those of the prior commercial Kimmell filter, but over an increased range of cavae sizes There is no proximal migration, even when severe mechanical forces are applied, nor distal migration, beyond the range exhibited by the prior commercial Kimmell filter. Radial penetration through adventitia is also within limits that have been acceptable historically. Further, it is believed that the filter can be maintained in situ for extended periods (of at least 8–10 years) without loss of the original chemical and mechanical properties, and with no corrosion, fatigue, or yielding, under even severe mechanical strain, and even in large diameter megacavae, e.g., up to 30 mm in diameter.

Other features and advantages of the invention will be apparent from the following description of the preferred embodiment, and from the claims.

DESCRIPTION OF THE PREFERRED EMBODIMENT

The drawings will first briefly be described.

Drawings

Prior Art

Figure 1:
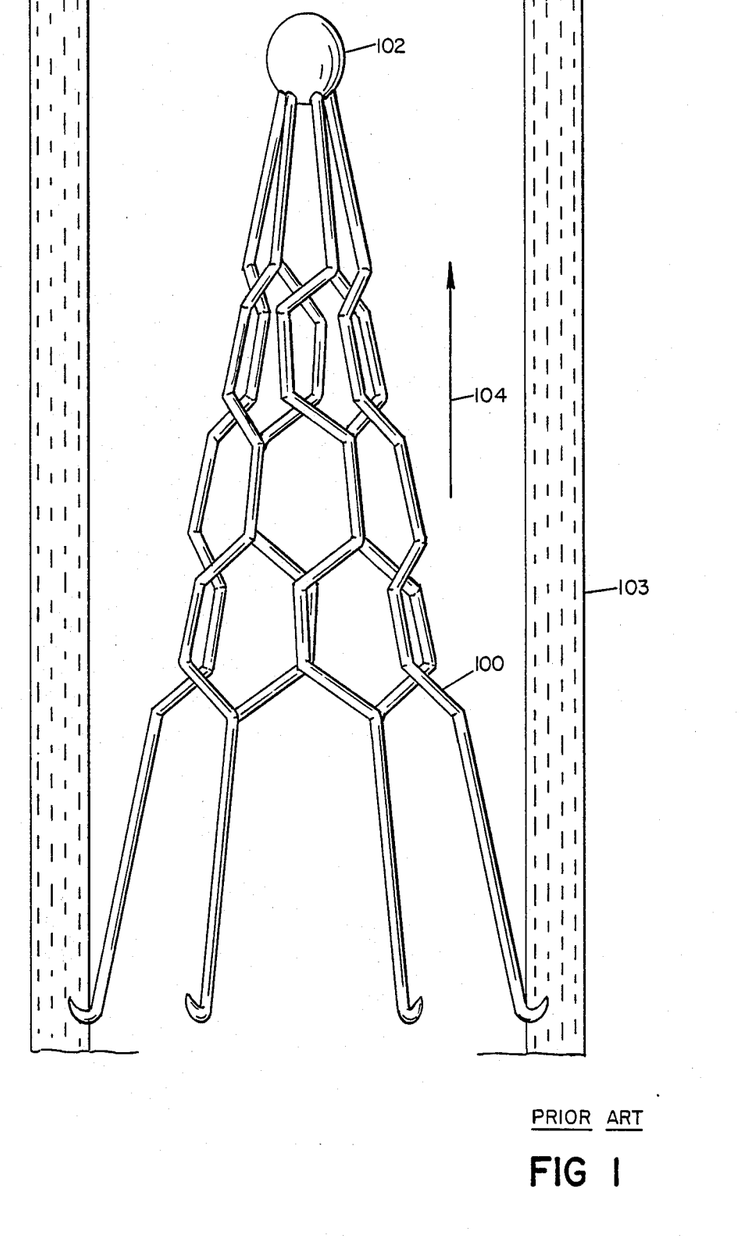
FIG. 1 is a diagrammatic representation of a prior art filter as described in Kimmell U.S. Pat. No. 3,952,747, in situ.
Figure 2:
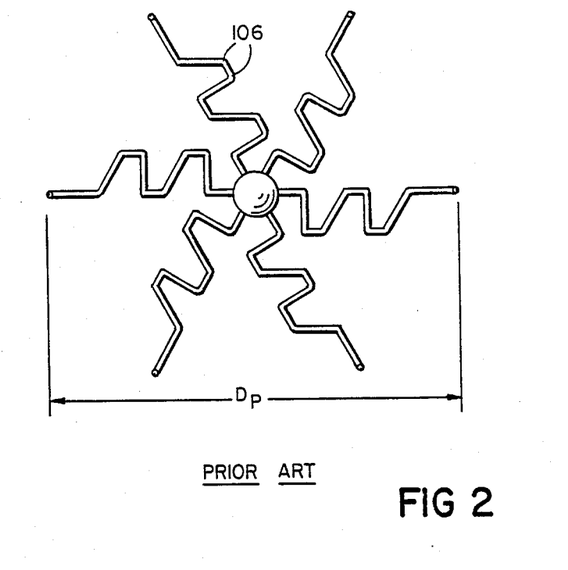
FIG. 2 is a plan view of the prior art Kimmell filter observed from above the head.

The prior art filter described in Kimmell U.S. Pat. No. 3,952,747, incorporated herein by reference, is shown in FIGS. 1 and 2. Briefly, the prior art Kimmell filter has six legs 100 which are squeeze-fitted into a large head or nose cone 102, all made from stainless steel. This filter has been inserted percutaneously using a 24 French catheter but usually has been inserted surgically. It is shown positioned in a cava 103, of diameter about 20 mm, with head 102 downstream relative to blood flow, shown by arrow 104. The leg bends, such as shown by number 106, and their positioning are shown in FIG. 2.

Structure of the Preferred Embodiment

Figure 3:
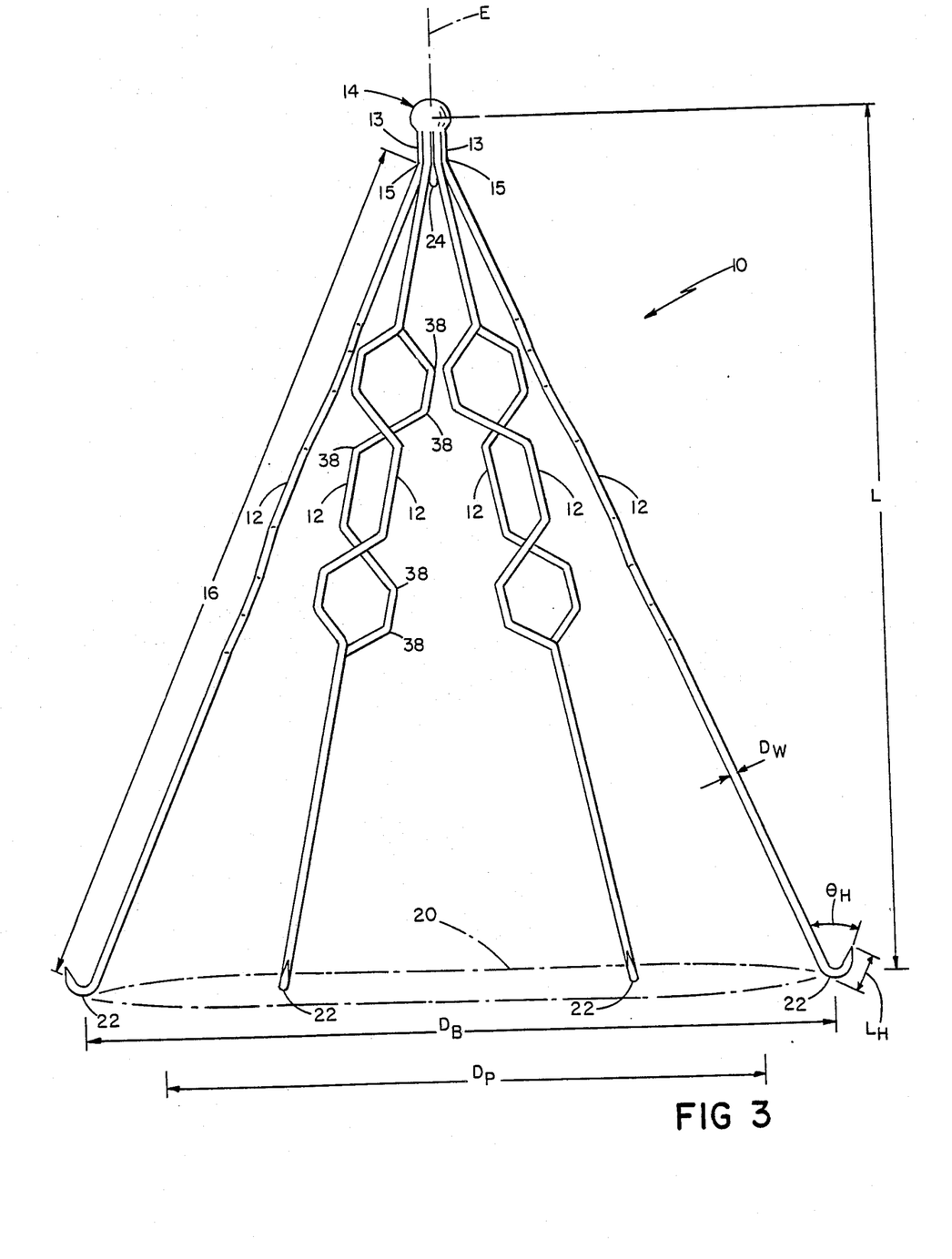
FIG. 3 is a side view of a preferred embodiment of the blood clot filtration device of the present invention.
Figure 4:
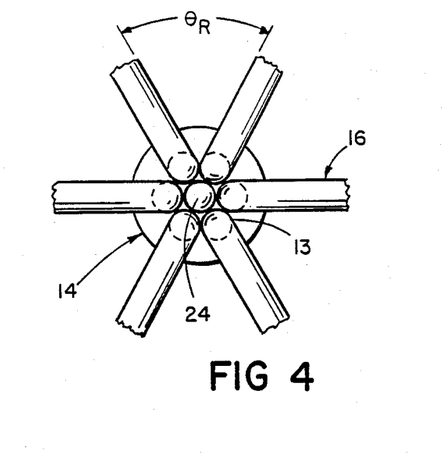
FIGS. 4 and 5 are plan and side views respectively of the head area of the device.
Figure 5:
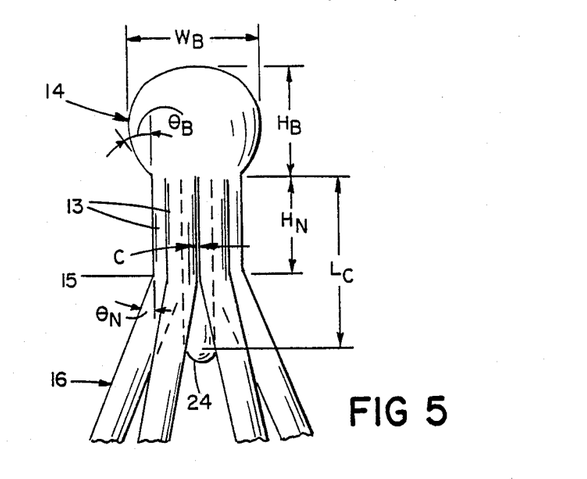

Referring to FIGS. 3, 4 and 5, the preferred embodiment of the blood clot filtration device 10 of the invention consists of six legs 12 protruding from a head or nosebead 14, both being of biocompatible titanium alloy beta III (ASTM grade 10, obtained from Ormco Corporation of Glendora, Calif., and designated Ti-11.5Mo-6Zr-4.5Sn, with major alloy elements molybdenum (10–13%), Zirconium (4.5–7.5%) and Tin (3.75–5.25%)). The legs 12, e.g., wire of diameter $D_W$, about 0.018 inch (0.5 mm), each have: a first linear leg portion 13 lying parallel to axis E of the filter, for distance $H_N$, e.g., about 1 mm, a nose bend 15, a second multi angled leg portion 16 of relatively greater length than the first linear leg portion, angling outwardly from the distal end of the first leg portion away from axis E, to define, with other second leg portions, an imaginary cone with base 20, shown as dotted lines; and outwardly directed hooks 22. The second leg portions 16 consist of a series of discrete linear segments arrayed generally tangent to the surface of the imaginary cone in a manner to increase the efficiency of the filtering effect. The diameter of the base of the filter is $D_B$, about 38 mm, and the overall length of the filter is L, about 50 mm. The linear leg portions 13 of all of the legs are closely arranged in a hexagonal pattern about central leg stub or segment 24 and the ends of all of these legs are joined at the apex in proximal head or nose bead 14, formed by fusing the ends of legs 12 and central leg stub 24 together.

Figure 6:
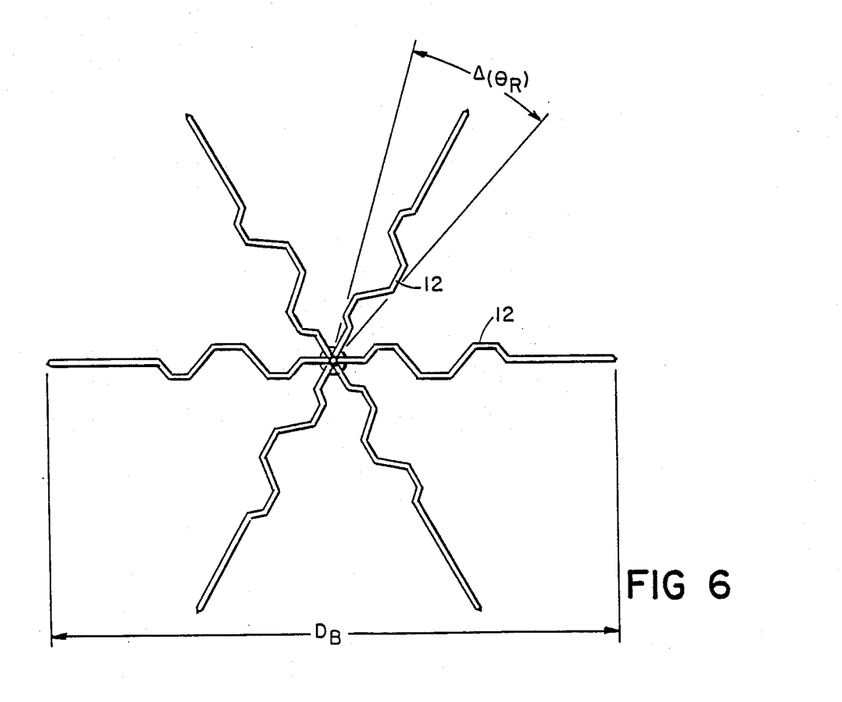
FIG. 6 is a plan view of the device, observed from below the head.
Figure 7:
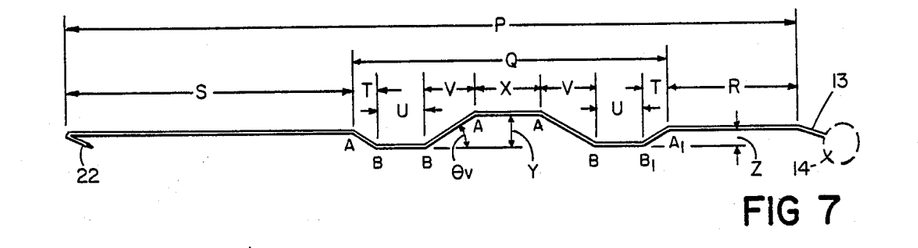
FIG. 7 is a diagrammatic representation of one leg of the device.

Referring to FIG. 4, the six legs 16 are located at angle $\theta_R$ apart, about 60°, with maximum clearance between the wires, e.g. about 0.002 inch (0.05 mm). The width of the resulting nose is $W_N$ about 0.06 inch (1.5 mm). Nose bead angle $\theta_N$ at nose bend 15 is about 23° and bead reinforcement angle $\theta_B$ is less than 35°. Referring to FIGS. 6 and 7, leg 12 has maximum extensions $\Delta$ ($\theta_R$) of about 13°. The minimum radial distance from nose bead 14 to first concave edge $A_1$ is 0.03 inch (1.66 mm) and to first convex edge $B_1$ is about 0.08 inch (2.0 mm). Total leg length P is about 1.85 inch (47 mm), and total bent span Q is about e.g., 0.85 inch (22 mm). Unbent lengths R and S are about 0.32 inch, and 0.72 inch (8.13 and 18.29 mm), respectively, and regions T, U, V, and X about 0.66, 0.12, 0.13, and 0.16 inch (16.7, 3.05, 3.3 and 4.06 mm), respectively, with angle $\theta_V$ about 40°. Distances Y and Z are respectively about 0.11 and 0.055 inch (2.79 and 1.40 mm).

Referring to FIG. 3, nose bead 14 of percutaneous filter 10 is formed by the molten metal of six legs 12 and leg stub 24 as they melt. Leg stub 24 is of length $L_c$, for example, about 2 mm. The six legs and leg stub are held in a fixture and are fused (e.g., by cast or arc welding) at the point where the legs meet, so that, under the influence of surface tension, the legs melt to form a small, solid spherical bead 14. The nose bead has a diameter $W_B$, about 2 mm, and height $H_B$, about 0.07 inch (1.8 mm).

The wires forming legs 12 are formed into first linear portion 13, second multi angled portion 16 and hook 22 against a steel guide in such a way that there is an alternating bend circumferentially oriented to produce a characteristic conical structure. Hook 22 has length $L_H$, about 1.8 mm, and is angled at angle $\theta_H$, about 34°. The bends 38 in leg wires 12 are formed by bending the wires at an angle of 130°–150°. Hook 22 is formed mechanically by bending the distal end of wire 12 over a mandrel. Hook 22 is then sharpened on three sides against an abrasive wheel. Nose bend 15 is made to form first linear portion 13 near to bead 14, parallel to axis E of filter 10. The leg 12 then bends slightly outwardly on the major angle of the cone and passes through a series of bends as described above.

Diameter $D_B$ and the length of first linear portion 13, from nose bend 15 to nose 14, as so determined, allows the filter to fit into a small diameter carrier tube, e.g., of approximately 12 French (inner diameter of about 3.7 mm), and still be able to spring open to the full diameter of the appropriate cava (10–30 mm). Diameter D and length A of the first linear portion 13 are selected relative to the overall length of the filter and the desired base diameter so the legs have sufficient spring force to engage the wall of the cava, but with force not so strong as to present a danger of rupture to the cava. If bead 14 and hook 22 are regarded as two ends of a beam, by selecting an appropriate distance $H_N$, e.g., about 1 mm, movement of hook 22 towards axis E, e.g., in compressing the filter for insertion into the blood vessel with a small diameter cartridge, applies stress to both nose bend 15 and the site of attachment of leg 12 to nose bead 14. Due to the arrangement shown, the stress is distributed over a large area, and the likelihood of permanent deformation is made less than in prior art filter devices. (Were the metal to yield the filter might become too small in diameter to engage the walls of a cava at all.)

Figure 8A:
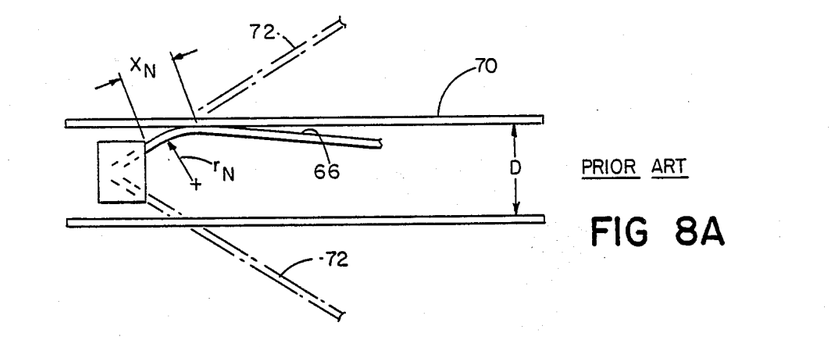
FIGS. 8a and 8b are diagrammatic representations of the strain on a leg in the prior art device and the present invention, respectively.
Figure 8B:
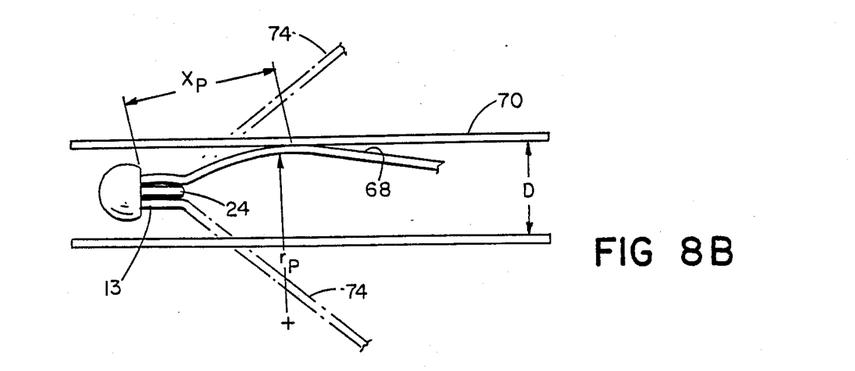

One of the advantages of nose extension 13 is illustrated in FIGS. 8A and B. FIG. 8A represents a filter compressed within a tube without extension 13, FIG. 8B similarly represents a filter with extension 13. Referring to the figures, solid lines 66 and 68 inside tube 70, of inner diameter, D, about 11 French, represent the filter legs when bent to fit into tube 70; dotted lines 72, 74 outside the tube represent the filter in its non compressed configuration. The corresponding lever arms $X_N$ and $X_P$ and radii of curvature $r_N$ and $r_P$ are shown. Without extension 13, $X_N$ and $r_N$ are small and thus compressive forces on bent wire 66 are great, and distortion of the wire is likely. With extension 13, $X_P$ and $r_P$ are large and the forces on wire 68 are small, with little chance of permanently deforming the wire. Shear and bending stresses are much lower for FIG. 8B than FIG. 8A, so yielding of wire 68 is unlikely.

Figure 9:
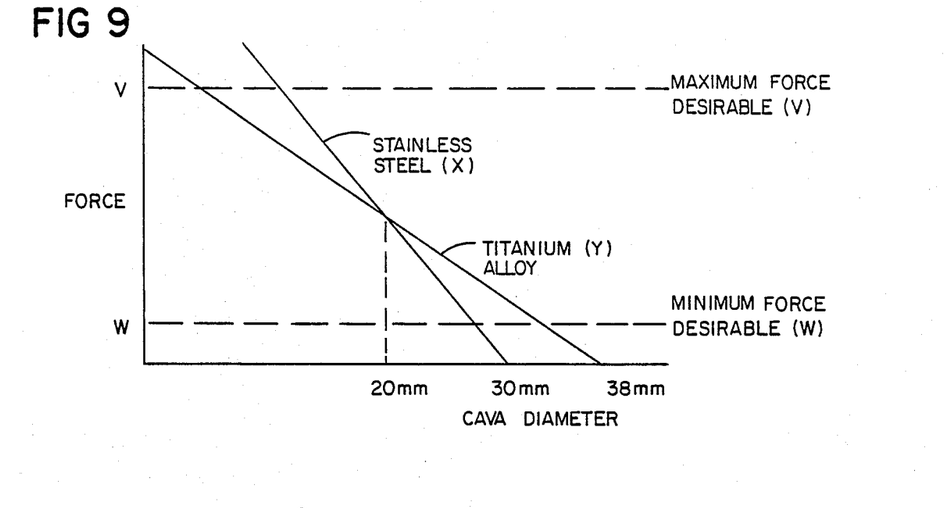
FIG. 9 is a diagrammatic representation of the relationship between force exerted by filters of the invention and prior art filters, on a vena cava wall versus cava diameter.
Figure 9A:
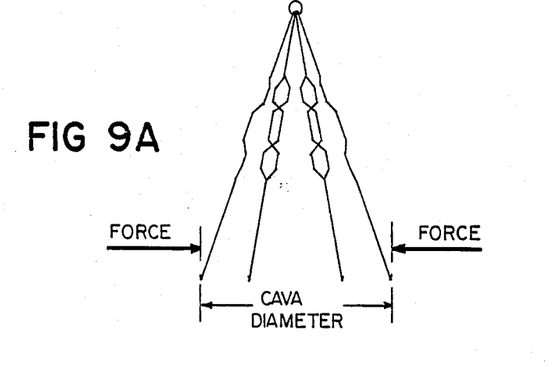
FIG. 9a is a diagrammatic representation of the filter of the invention illustrating points of stress exerted on a cava.

The titanium alloy used to construct the preferred embodiment has about three times as much elasticity as other possible alloys such as stainless steel and thus help to avoid unwanted permanent deformation. Referring to FIG. 9, curves X and Y describe the relationship between stress exerted upon tissue by a stainless steel filter (curve X) and a titanium filter (curve Y) and the cava diameter in which the filter is placed (FIG. 9a). Both curves roughly describe a straight line intercepting at the optimal stress value in an average cava diameter of 20 mm. From FIG. 9, it can be calculated that if a stainless steel filter of an initial diameter of about 30 mm were released into a cava whose diameter were 30 mm, it would rest there without exerting any stress on the cava wall. As the size of the cava decreases in diameter, the force on the cava wall would increase linearly. In contrast, the equivalent titanium filter of the present invention has a resting diameter of about 38 millimeters. The curve relating force to the diameter of the filter at rest is also a straight line (curve Y, FIG. 9), but one which is less steep than that for stainless steel. The limits to the force that can be exerted against a cava are shown at points V, W in FIG. 9. If the force exerted by a filter on a cava is on the low side, the filter would be less secure against incidental movement, e.g., due to movement by the patient or due to an embolism caught in the filter. If the force is on the high side, there is a risk of perforation of the wall of the cava by the filter. The advantage of the titanium filter is that, because its resting diameter is greater, it exceeds the desirable minimum force earlier than the stainless steel filter and thus can be used for larger cava than stainless steel filters. On the other hand, when the titanum filter is in a smaller cava, it exerts less force than the stainless steel filter on the walls of the cava. Thus, there is less risk of perforation of smaller cava diameters.

A further advantage of the titanium alloy filter is that it has a high tolerance to mechanical strain. This allows a filter of the invention to be inserted into a cartridge of smaller diameter than the equivalent prior art stainless steel filter, and thus inserted into a cava using a narrower catheter. Thus, the filter of the invention can be readily inserted percutaneously.

Figure 10:
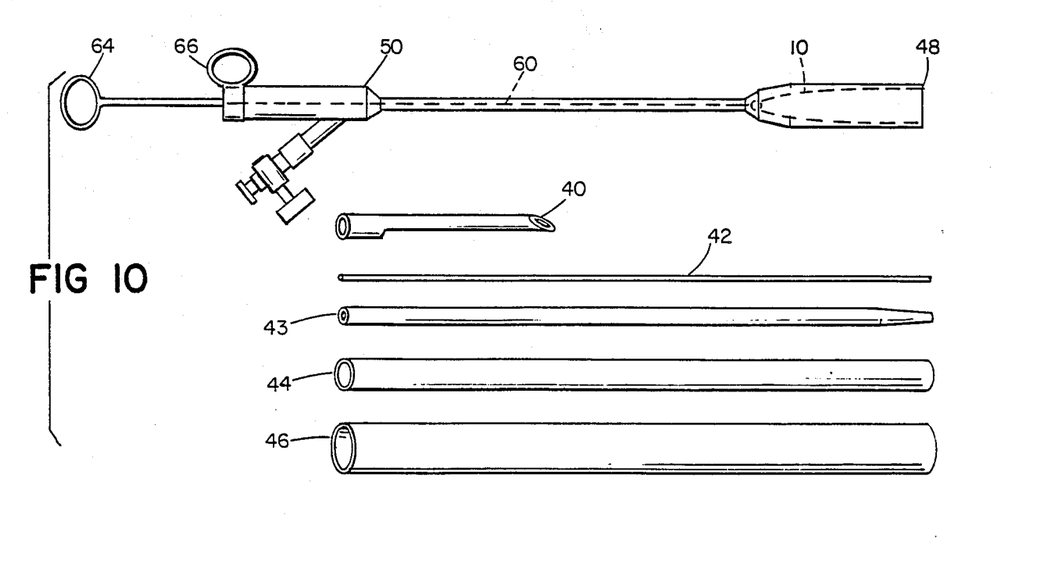
FIG. 10 is a diagrammatic plan view of a kit for inserting the filtration device of the invention percutaneously.

Referring to FIG. 10, a kit for percutaneous insertion of the filtration device of the invention includes a guidewire 42, catheters 43, 44, sheath 46 and needle 40 For percutaneous insertion, the vein is punctured with needle 40. Guidewire 42 is inserted into the vessel through the needle. Tapered catheter 43, up to 8 French in diameter, is pushed into the vein, over the guide wire. Slightly larger catheter 44, up to 10 to 12 French, is slid coaxially over the first and is used to dilate the tissue and the vein. A tapered catheter, with a thin-walled sheath 46, is then placed over this catheter and the inner catheters and guidewire removed, leaving the sheath behind. The sheath acts as an access to permit the insertion of a cartridge 48 holding the filter 52. Sheath 46 has a thin wall so that catheter 44 fits snugly inside of sheath 46 and they can travel together as a single unit. Sheath 46 is constructed of high density polyethylene and is slippery so that the friction between it and the cava is reduced. Cartridge 48 with filter 10 is introduced through sheath 46. Sheath 46 should be flexible enough so that it doesn't kink, with, e.g., an inside dimension of 12.6 French and an outside dimension between 13 and 14 French. Also provided in the kit is a filter delivery system 50 for delivery of the catheter. The dotted line within cartridge 4 shows the orientation of the filter 10, in the orientation where the hooks are ready to come out first, i.e., for introduction into a jugular vein. Pusher 60 is solid and is used to discharge the filter into location in a cava. Once the filter in the sleeve is in an appropriate position, the filter is pushed out of the sleeve using pusher 60. The legs of the filter will spring outward and engage the cava walls, thus holding the filter in position.

Comparison with Prior Commercial Kimmell Filter

The percutaneous filter of this invention can achieve a filter mesh between 75% and 125% of that of the prior commercial Kimmell filter, when both are confined inside a 20 mm inner diameter cylinder, with equivalent orientation (filter axis to cylinder axis). The leg wires are thus able to filter blood passing through the filter and catch clots of a desired size.

The range of arc $\Delta(\theta_R)$ (FIG. 6) described by the most proximal set of legwire bends is preferably reduced to less than 80% of $\Delta(\theta_R)$ for the corresponding bends in the prior commercial Kimmell filter. This reduces legwire interferences that otherwise would impose large flexural strains at the head of the filter during leading into the narrow-bore (e.g., 3.7 mm inner diameter) carrier 48. The flexural elasticity (resilience) achievable by this filter is at least 40% greater than that of the prior commercial Kimmell filter, for example, the flexural yield strain of the legwire alloy is preferably greater than 1.8%, as in high yield strain titanium alloys. This latter feature enables bending the filter legs towards the central axis, E (FIG. 3), by at least 21.6°, whilst the prior commercial Kimmell filter legs are bent in by only about 15.0°, during loading. Moreover, the legwire alloy has a linear (i.e., a proportional or elastic) relationship of stress vs. strain extending to above 1% deformation. That is, the legwire alloy remains elastic even during, for example, elongation by more than 1%.

The maximum strain concentration in the percutaneous filter structure (during loading, and when the filter is within a cava) can be significantly lower than that in the structure of the prior commercial Kimmell filter. The strain concentration at the proximal end of the filter legs is achieved by, a filter nose (13, in FIG. 3), of minimal height $H_N$ (FIG. 3), and a filter bead (14, in FIG. 3); the bead reinforcement angle $\theta_B$ (FIG. 3) is preferably reduced below the nose-cone "reinforcement angle" of 90° found in the prior commercial Kimmell filter; the maximum clearance C (FIG. 3) between nose-wires is minimized; and the close-packed center wire (leg stub 24, in FIG. 5) maintains the alignment of the array of wires and serves as an advantageous fulcrum during deflection, helping to reduce stress, to avoid yielding during maximum compression. Furthermore, the six filter legs may be negatively curved so that the cone shape described by the legs is slightly concave (cusp-like). Upon insertion into a 20 mm vena cava, the slight concave bend is effectively straightened out.

In order to insure long term mechanical stability and safe anchorage in normal vena cava (having a diameter of about 20 mm) or larger megacavae, the invention achieves anchoring dilational loads and forces at the hook tips similar to those produced by the prior commercial Kimmell filter in normal cava. Preferably, the filter base diameter $D_B$ (FIG. 3) is 30–50 mm (typically 38 mm), compared to diameter $D_P$ of the prior commercial Kimmell filter, e.g., about 30 mm.

A low modulus alloy is important to optimally satisfy the above requirements preferably one which resists corrosion and fatigue, even after severe cold-forming or hot-forming and cold-joining or hot-joining operations.

Other embodiments are within the following claims.

What is claimed is:

1. In a blood clot filtration device for filtering solid and semi-solid materials from a liquid moving along a vessel axis of a tubular vessel, said filtration device having a device axis and comprising:
   a head; and
   a plurality of legs having divergent leg portions, each said leg secured at one of its ends to said head and each having securing means on its end distal with respect to said head; and at least one generally U-shaped bend intermediate its end,
   the improvement wherein,
   said legs further comprises a first linear leg portion between said head and said divergent leg portion, said first linear leg portion having a predetermined length emanating distally from said head and, said first linear leg portion being arranged parallel to said device axis of said filtration device.

2. In a blood clot filtration device for filtering solid and semi solid materials from a liquid moving axially in a tubular vessel, said filtration device comprising;
   a head; and
   a plurality of legs having divergent leg portions, each said leg secured at one of its ends to said head and each having securing means on its end distal with respect to said head; and at least one generally U-shaped bend intermediate its end;
   the improvement wherein,
   each of said legs further comprises a first leg portion between said head and its divergent leg portions, said first leg portions closely surrounding a central member, said head formed of the ends of said first leg portions and the end of said central member, said central member serving to provide lateral support to said first portions emanating from said head when said legs are compressed together.

3. The blood clot filtration device of claim 1 or 2 wherein said legs and said head are formed of a titanium alloy.

4. The blood clot filtration device of claim 3 wherein said alloy is at least 50 percent by weight titanium.

5. The blood clot filtration device of claim 1 or 2 wherein said head comprises a bead formed by fusing said legs.

6. The blood clot filtration device of claim 1 or 2 wherein the legs at said head closely surround a central wire segment.

7. The blood clot filtration device of claim 4 or 6 wherein the diameter of said bead forming said head is of the order of less than about 3 mm.

8. The blood clot filtration device of claim 1 or 6 wherein the diameter of the base of said conical aspect of said device measured at the intersection of said second, multi-layered leg portions and said hook portions is between about 30 and 50 mm.

9. The blood clot filtration device of claim 7 wherein said device is adapted to be introduced into said blood vessel within a cylindrical cavity of an introducing cartridge, said cavity within which said device is disposed for insertion having an inner diameter between about 3 to 4 mm.

10. A blood clot filtration device adapted for implantation percutaneously, of the kind for preventing movement of blood clots within a blood vessel comprising:
a head and a plurality of legs extending therefrom,
said head comprising a bead formed by fusing said legs,
said legs comprising:
(a) a first linear leg portion of predetermined length emanating distally from said head in a direction upstream of the direction of blood clot movement within said vessel, said first linear leg portion arranged generally parallel to the axis of said device,
(b) a second, multi-angled leg portion of relatively greater length than said first linear leg portion, said second, multi-angled leg portion extending generally outwardly from the distal end of said first linear leg portion, at an acute angle to said axis to form, with said second, multi-angled leg portions of other legs, a conical aspect, said second, multi-angled leg portion comprising a series of discrete linear segments arrayed generally tangent to a cone defined by the set of said second, multi-angled leg portions, and
(c) a hook portion at the distal end of each said leg extending outwardly, away from said axis, in a manner for engaging the blood vessel wall to fix the position of said device therewithin, and
said legs and said head being formed of a titanium alloy.

11. The blood clot filtration device of claim 1 or 7 wherein said length of said first linear leg portion is of the order of about 0.5 to 2 mm.

12. The blood clot filtration device of claim 1 or 7 wherein the overall length of said device along the axis, within said blood vessel, is of the order of about 50 mm.

13. A blood clot filtration device adapted for implantation percutaneously via a tubular cavity of an introducing cartridge, into a blood vessel of the body, of the kind for preventing movement of blood clots within said blood vessel, said cavity within which said device is disposed for insertion having an inner diameter of the order of between 2 to 4 mm, said filtration device comprising:
a head and a plurality of legs extending therefrom,
said head comprising a bead formed by fusing said legs and having a diameter of the order of less than about 3 mm,
said legs comprising:
(a) a first linear leg portion of predetermined length emanating distally from said head in a direction upstream of the direction of blood clot movement within said vessel, said first linear leg portion arranged generally parallel to the axis of said device, said predetermined length being of the order of about 0.5 to 2 mm,
(b) a second multi-angled leg portion of relatively greater length than said first linear leg portion, said second, multi-angled leg portion extending generally outwardly from the distal end of said first linear leg portion, at an acute angle to said axis to form, with second, multi angled leg portions of other legs, a conical aspect having a diameter at the base of between about 28 and 48 mm, said second, multi-angled leg portion comprising a series of discrete linear segments arrayed generally tangent to said cone defined by said second, multi-angled leg portions, and
(c) a hook portion at the distal end of each said leg extending outwardly, away from said axis, in a manner for engaging the blood vessel wall to fix the position of said device therewithin, and
said legs and said body being formed of a titanium alloy,
the overall axial length of said device in position within said blood vessel being of the order of about 50 mm.

14. The device of claim 6, 7, or 13 wherein said device further comprises a central wire segment positioned axially, with said first linear leg portions disposed thereabout.

15. In a blood clot filtration device for filtering solid and semi-solid materials from a liquid moving axially in a tubular vessel, said filtration device comprising:
a head; and
a plurality of legs having divergent leg portions, each said leg secured at one of its ends to said head and each having securing means on its end distal with respect to said head; and at least one general U-shaped bend intermediate its ends, the legs being formed of a high strength titanium alloy having a linear relationship of stress versus strain extending to above 1 percent deformation of said alloy, and said head being formed by fusing together corresponding ends of the legs, said legs, under a no-stress condition, conforming to a large base cone of diameter of about 30 mm or more, the legs being capable of such elastic deformation that the filter can be collapsed into a capsule of about 12 French external diameter.

16. The filter of claim 15 wherein the base diameter to which the ends of the legs conform is 30 mm or larger.

17. The filter of claim 15 wherein said blood clot filtration device exerts a force against the tubular vessel when in place therein, said tubular vessel having a predetermined maximum force limit, said titanium alloy having an elasticity selected to exert less than said maximum force against said tubular vessel for a tubular vessel inner diameter substantially less than 20 mm.

18. In a blood clot filtration device for filtering solid and semi-solid materials from a liquid moving axially in a tubular vessel, said filtration device comprising;
a head; and
a plurality of legs having divergent leg portions, each said leg secured at one of its ends to said head and each having securing means on its end distal with respect to said head; and at least one generally U-shaped bend intermediate its ends, the legs being formed of a high strength titanium alloy having a flexural yield strain greater than 1.8%, and said head being formed by fusing corresponding ends of the legs, said legs, under a no-stress condition, conforming to a large base cone of diameter of about 30 mm or more, the legs being capable of such elastic deformation that the filter can be collapsed into a capsule of about 12 French external diameter.

* * * * *